April 7, 1936. F. W. ANDERSON Plant Pat. 173

NECTARINE

Filed Nov. 25, 1935

INVENTOR

F. W. Anderson

BY

ATTORNEY

Patented Apr. 7, 1936

Plant Pat. 173

UNITED STATES PATENT OFFICE

173

NECTARINE

Frederic W. Anderson, Merced, Calif.

Application November 25, 1935, Serial No. 51,462

1 Claim. (Cl. 47—62)

This invention relates generally to nectarines, and is directed in particular to a yellow fleshed nectarine. Heretofore yellow fleshed nectarines have not been of any appreciable commercial value due to the fact that the fruit is relatively small and the flesh is soft. The cultivation of nectarines has therefore not been practicable because the fruits have been too delicate to meet the demands of commerce.

The principal object of my invention is to provide a hardy yellow fleshed nectarine of large size and firm flesh and which has an early ripening period. Due to these characteristics my improved nectarine is especially adapted for canning, drying and marketing purposes.

The nectarine herein described was produced at Le Grand, California in the following manner:

A cross was made on J. H. Hale peach blossoms with Lippiat nectarine pollen in the spring of 1924. The resultant progeny of this pollinization were all yellow fleshed free-stone peaches. These peaches were open pollinated and several hundred seeds planted. Approximately one-fourth of their progeny were yellow fleshed nectarines of which the nectarine described in this specification ripens the earliest, is of the greatest promise commercially, and has been successfully asexually reproduced.

In the annexed drawing, Figure 1 is a perspective view of my nectarine.

Figure 1:
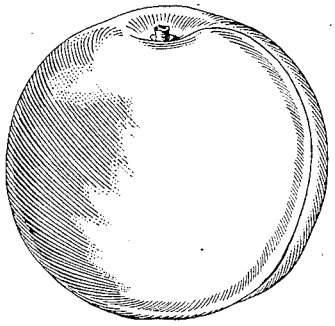
Figure 3:
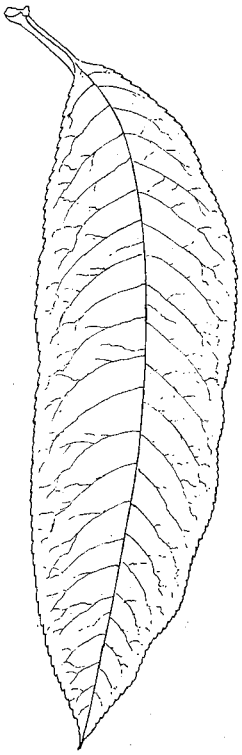
Figure 3 is a perspective view of a leaf of the nectarine tree described herein.
Figure 2:
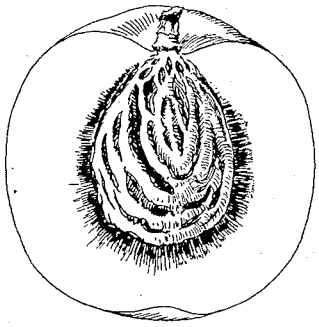
Figure 2 is a sectional view taken axially of the fruit and with the stone remaining in place.

Referring now in more detail to the characteristics of the tree and its fruit:

*Tree.*—The tree is large and vigorous as well as being spreading and open, vase-formed, very productive and a regular bearer. The trunk of the tree is medium in size while the branches are of medium size and a glossy brown color. The lenticels are of medium size and number.

*Leaves.*—The leaves are large and thick, averaging 6 inches in length and 1¾ inches in width. They are eglandular, dark green in color, and smooth in texture. The margins of the leaves are finely serrated, the petiole is of medium size and length, and there are no glands.

*Flower buds and flowers.*—The flower buds are conic, of medium size and length and the flowers are large, pink, and bloom substantially at the same time as other varieties of nectarines.

*Fruit.*—The fruit is of large uniform size, symmetrical, globose in shape, and has a shallow suture. The fruit averages 2½ inches in diameter axially, 2⅜ inches transversely in the suture plane, and 2⅜ inches transversely at right angles to the suture plane. The cavity and base are rounded and the apex is depressed. The stem is medium in length, glabrous and its adherence to the stone is strong. The skin of the fruit is of medium thickness and toughness, free from the flesh, has a slight tendency to crack, its color is red on a yellow background, and down on the skin is wanting. The flesh of the fruit is yellow, mottled with red next to the stone. The surface of the pit cavity is red mottled with yellow and pink fibers. The fruit is moderately juicy, firm and meaty in texture, the fibers are few, fine and tender, the flavor is acid, the aroma is distinct, and the eating qualities of the fruit are good.

The stone of the fruit is free, of medium size, globose in form, straight at the base, oval at the hilum, and rounded at the apex. The sides of the stone are equal, irregularly furrowed and pitted near the base throughout and the ridges are jagged toward the apex. The pits are elongated, the ventral edge is thick without wing toward the base, the dorsal edge is full with a shallow broad groove throughout, and the ridges are interrupted. The stone is reddish yellow in color.

*Ripening period.*—The nectarine described herein ripens from one week to ten days earlier than the Elberta peach and approximately two weeks earlier than the Lippiat nectarine. Picking of the fruit normally extends from July 7 to July 28 although these dates may vary somewhat due to seasonal conditions.

Further compared with the Lippiat nectarine my improved nectarine is much larger in size and firmer in flesh, although retaining the yellow colored flesh of the Lippiat. The keeping quality of the fruit is also good. These characteristics make my nectarine much more suitable for drying, canning and shipping.

The above described characteristics may of course vary to some degree depending on soil and climatic conditions.

Having thus described my invention, what I claim as new and useful and desire to secure by Letters Patent is:

The nectarine herein described characterized by its size, firmness of flesh and early ripening period relative to the Lippiat nectarine.

FREDERIC W. ANDERSON.